United States Patent [19]

Westfall et al.

[11] Patent Number: 4,716,032

[45] Date of Patent: Dec. 29, 1987

[54] AEROSOL SPRAY COMPOSITION FOR MASTITIS PREVENTION

[75] Inventors: Geoffrey J. Westfall, P.O. Box 285, Rte. 6, Brooklyn, Conn. 06234; Franklin D. Haase, Ridge Farm, Ill.

[73] Assignee: Geoffrey J. Westfall, Brooklyn, Conn.

[21] Appl. No.: 764,751

[22] Filed: Aug. 12, 1985

Related U.S. Application Data

[62] Division of Ser. No. 519,909, Aug. 3, 1983, Pat. No. 4,548,807.

[51] Int. Cl.$^4$ .............................................. A61K 9/12
[52] U.S. Cl. ..................................... 424/45; 424/43; 222/3
[58] Field of Search ............................ 424/45, 43, 7.1

[56] References Cited

U.S. PATENT DOCUMENTS

| | | | |
|---|---|---|---|
| 2,496,270 | 2/1950 | Coler | 424/7.1 |
| 3,135,658 | 6/1964 | Hanus et al. | 424/45 |
| 3,144,386 | 8/1964 | Brightenback | 424/45 |
| 3,427,377 | 2/1969 | Bauer et al. | 424/7.1 |
| 3,928,556 | 12/1975 | Sweger | 424/45 |
| 4,382,078 | 5/1983 | Berkhoff et al. | 424/45 |

FOREIGN PATENT DOCUMENTS 1026831  4/1966  United Kingdom ................. 424/45

OTHER PUBLICATIONS

Kirk-Othmer-Encyclo. Chem. Technol. vol. 16 (1968) p. 860.
National Mastitis Council-22nd Meeting, Feb. 21-23, 1983, pp. 52-59 & 78.
McGraw-Hill Encyclopedia of Chemistry (1983), p. 848.

Primary Examiner—Sam Rosen
Attorney, Agent, or Firm—Nies, Webner, Kurz & Bergert

[57] ABSTRACT

A method, composition and containerized product for use in preventing the disease of mastitis in dairy cows and other animals. The invention employs a homogeneous disinfectant composition in the form of an aerosol spray which applies disinfectant to the teat while at the same time chilling the teat, particularly at the lower end where the teat sphincter muscle is located. Use of the present disinfectant composition, which contains an aerosol propellant such as dimethyl ether, results in chilling temperatures of about 25° to 35° F. being attained on the exterior surface and orifice end of the teat. By such treatment, the teat sphincter is caused to contract and close the teat orifice, thus reducing the incidence of infection.

15 Claims, 8 Drawing Figures

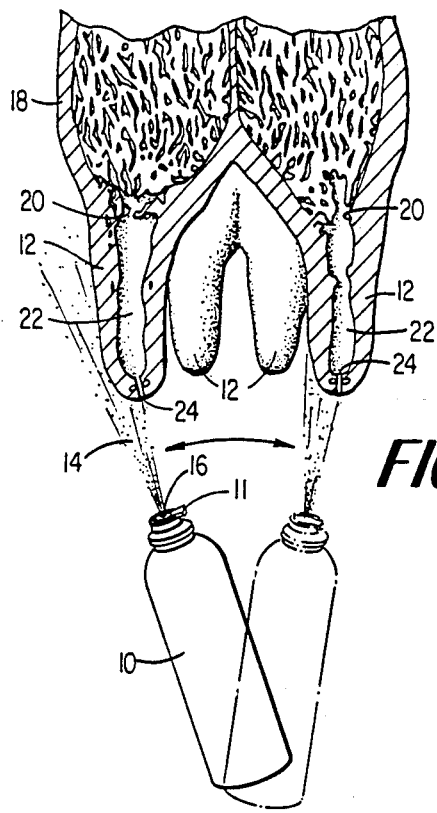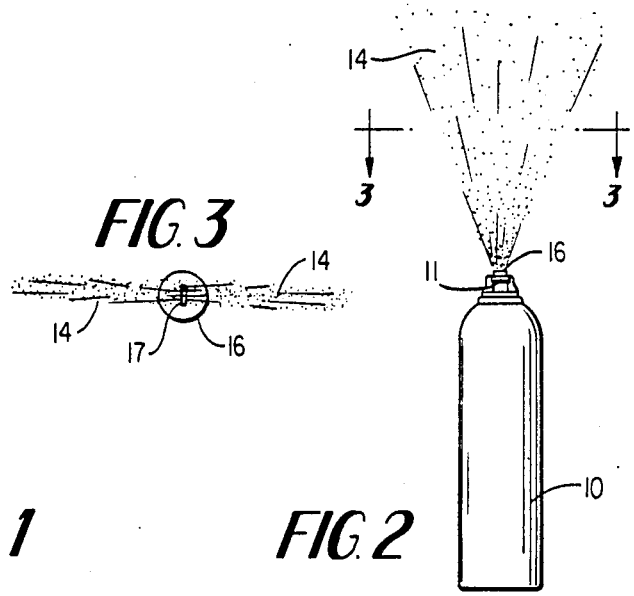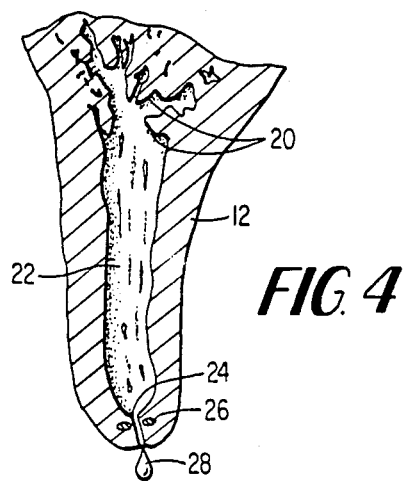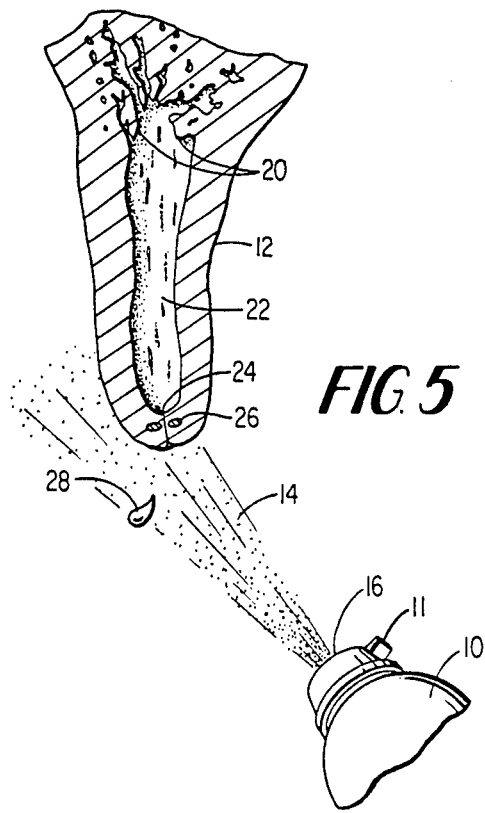

AEROSOL SPRAY COMPOSITION FOR MASTITIS PREVENTION

This is a division of application Ser. No. 519,909, filed Aug. 3, 1983, now U.S. Pat. No. 4,548,807.

BACKGROUND AND SUMMARY OF THE INVENTION

The present invention relates to the prevention of mastitis, a mammary gland infection, in dairy cattle and other animals. More particularly, the present invention relates to a method of treating the teats of dairy cattle after milking for the purpose of preventing mastitis. Also disclosed are a disinfectant composition as well as a container and valve construction for use in such treatment.

Previous methods for reducing the incidence of mastitis in dairy cattle have included the practice of applying a disinfectant to each of the teats of the cow after milking by the use of a dip cup. The procedure generally includes filling the dip cup with a disinfectant and dipping each teat individually in the cup after milking. This procedure has been used for many years and has been universally recommended. However, there are disadvantages associated with such a procedure. In particular, the edge of the cup and the disinfectant itself may spread disease from one infected teat to another and from cow to cow. The cup can also be cumbersome to use and dipping all the teats takes additional time which dairy farmers do not have. Thus the dipping procedure is sometimes either omitted altogether or carried out in an improper manner.

By the present invention, there is provided a method for preventing mastitis by the use of a disinfectant composition in the form of an aerosol spray which applies disinfectant to the teat while at the same time chilling the teat, particuarly at the lower end where the teat sphincter muscle is located By such treatment, the teat sphincter is caused to contract and close the teat orifice, thus reducing the incidence of infection.

The use of the disinfectant in the form of an aerosol spray has many advantages, including: first, it is convenient and quickly available; second, most people accept and readily use such sprays so that the job of treatment with disinfectant is more likely to be carried out by the dairy farmer; third, the use of the aerosol container and spray will eliminate cross-contamination between teats and also between cows; fourth and very important, the particular aerosol spray composition which is employed produces the desired chilling effect on the teat.

The use of commercial milking machines tends to dilate or stretch the sphincter at the end of the teat, thus making it easier for infection to enter the mammary gland after milking. Chilling the end of the teat, however, promotes contraction of the sphincter and also reduces the inflammatory change that occurs in the tissue at the end of the teat from the repeated trauma of the milking machine. Reducing the trauma induced inflammation by chilling results in healthier tissue at the end of the teat and the healthier condition of the tissues helps in preventing infection from entering the mammary gland. Contraction of the sphincter by rapid chilling of the end of the teat closes the streak canal and further reduces the possibility of infectious organisms passing through the teat orifice into the mammary gland.

The present invention is distinguished from the procedure described in U.S. Pat. No. 3,144,386 to Brightenback, wherein an aerosol foam preparation is employed for the purpose of treating dairy cattle already infected with mastitis. In the prior art method, a medicinal preparation in the form of an aerosol foam is injected into the affected portion of the udder by the use of a cannula type applicator. Thus the Brightenback patent is not concerned with treatment of the exterior of the teats for the purpose of preventing infection.

The present invention is also distinguished from the procedure described in U.S. Pat. No. 3,648,696 to Keith, wherein the teats are sprayed with disinfectant by the use of a spray nozzle contained within a tubular shroud, the nozzle being connected by a conduit to a hand operated air pressurized mechanism for use in transmitting disinfectant to the nozzle. In this prior art device, there is no means for achieving the chilling effect which is necessary in order to obtain the desired effects of the present invention.

In a similar manner, the present invention is distinguished from the procedure described in U.S. Pat. No. 3,713,423 to Sparr, which is pressurized by air under pressure and no means are provided in this prior art device for obtaining the necessary chilling effect of the present invention.

In one embodiment of the present invention, the aerosol spray is provided in a pressurized container having a valve which allows the container to be held beneath the udder and near the teats and which can provide a suitable pattern of spray, preferably fan-shaped, which passes upwardly and outwardly in an axial direction from the container to cover the lower end of the teat with disinfectant and propellant, flash volatilization of the propellant chilling the lower end of the teat at the same time.

By the present method, only the spray with disinfectant touches the teat, thus eliminating the problems of crosscontamination between teats and the spread of infection from one cow to another as occurs in the dipping procedure. Also, the method of applying disinfectant under pressure in accordance with the present invention tends to blow away the residual milk at the end of the teat and to cause effervescence of the disinfectant which permits better contact of the disinfectant with the teat orifice.

The composition which is employed in the treatment of the present invention includes a combination of materials which has been found to be particularly useful in the prevention of mastitis. In particular, the composition provides the necessary disinfectant and chilling effect, while also maintaining a uniform mixture throughout the use of the contents of a pressurized container of the composition. In one embodiment, the composition of the present invention includes the following components: an aerosol propellant such as dimethyl ether; a disinfectant such as chlorhexidine; a lower alkanol such as ethanol; glycerine; a dye material; and water.

It is an object of the present invention to provide an improved method of treatment for preventing mastitis in dairy cattle.

It is a further object of the invention to provide a disinfectant composition which may be used in the form of an aerosol spray to effectively and rapidly chill the teats of dairy cattle as the disinfectant is applied so as to result in improved protection against mastitis.

It is another object of the invention to provide a specific composition having an appropriate propellant ratio in combination with a container and valve construction which is highly effective for use in applying a disinfectant in aerosol form to the teats of dairy cattle.

An additional object of the invention is to provide a method of reducing the adverse effects of commercial milking machines on the teats of dairy cattle.

A further object of the invention is to provide a method of preventing mastitis which is easy to use and readily accepted by dairy farmers.

Another object of the invention is to eliminate cross-contamination between the teats of a cow or between cows such as has been experienced with prior art methods employing a dip cup.

These and other objects will be more fully understood from the following detailed description taken with the accompanying drawings.

BRIEF DESCRIPTION OF THE DRAWINGS

FIG. 1 shows a schematic representation of the present invention in which an aerosol spray of disinfectant is applied with chilling to the teats of a dairy cow;

FIG. 2 is a view of the container similar to that seen in FIG. 1 but with the container rotated 90° and showing the preferred fan-shaped nature of the spray pattern;

FIG. 3 is an enlarged detail view taken on line 3—3 of FIG. 2 to illustrate the elongate slot-type nozzle orifice used to help accomplish the fan-shaped spray pattern;

FIG. 4 is an enlarged cross-section view of a teat at the finish of milking, the sphincter having relaxed leaving the streak canal and orifice open;

FIG. 5 is a view similar to that of FIG. 4, illustrating application of the disinfectant spray composition which blows away the residual milk droplet(s) and causes closing the streak canal and teat orifice.

DESCRIPTION OF THE PREFERRED EMBODIMENTS

Figure 6:
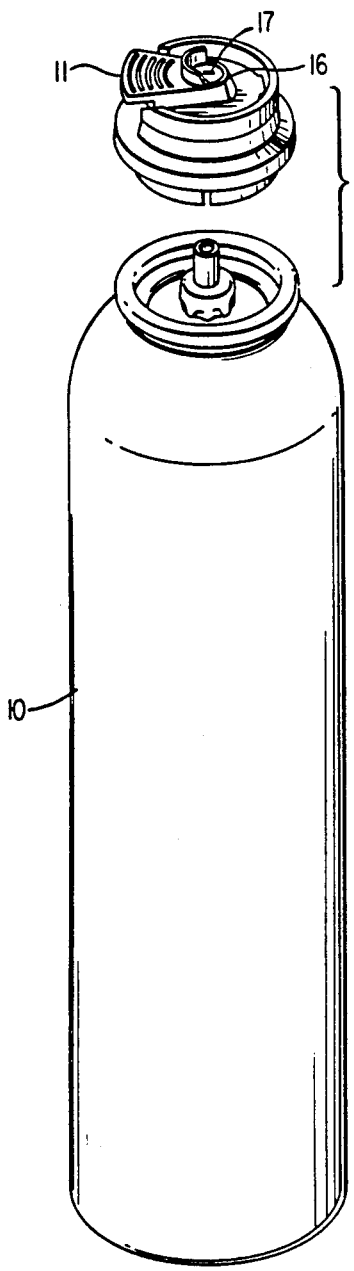
FIGS. 6, 7 and 8 illustrate an aerosol container and details of a prior art discharge valve and nozzle.

In the embodiment of the invention as illustrated in FIGS. 1 through 5, an aerosol container 10 which holds the composition of the present invention is provided, with the container 10 being shown in FIG. 1 in position directly beneath the udder and teats 12 of a dairy cow. The composition is shown as being projected upwardly in an axial direction from the container 10 in a fan-shaped spray pattern 14 by the use of a nozzle 16 as in FIG. 3 with an elongate slot type orifice 17. The distance between the nozzle 16 and the lower end of the teat 12 may be about 4 to 6 inches. The container 10 which includes the valving component and container cap 11 may be formed of aluminum or other suitable material such as tin-plate. Such container, with the valved cap and discharge control unit, are commercially available aerosol spray container components. Suitable valve, cap and discharge control are components which are well known, e.g., suitable such units being shown and described, for example, in U.S. Pat. Nos. 3,185,350; 3,260,416 and 3,967,763 all of which patents are incorporated herein by reference. The container may be lined with a coating such as plastic, if desired.

During the milking process, milk flows downwardly from the udder 18 into each individual teat 12 through a rosette of tissue 20 known as Furstenberg's rosette. The milk flows into the teat cistern 22 and then into the teat orifice 24 known as the streak canal where it passes out of the teat 12 in a flow controlled by the teat sphincter muscle 26.

As shown in FIG. 5, the application of the aerosol spray disinfectant composition with the chilling effect results in the contraction of the sphincter 26 as well as the teat orifice 24, as the cold spray 14 impacts the end of the teat 12, blows off the leaked milk droplet(s) 28, and inundates and penetrates the end of the teat and the orifice 24, thus further contributing to the prevention of mastitis as described herein.

The composition employed in the present invention includes an aerosol propellant such as dimethyl ether which functions as a carrier and low temperature-producing agent. The propellant component, which is preferably water and alcohol soluble, may be present in an amount of from about 5 to 75% by weight of the total composition. Dimethyl ether is the preferred propellant.

The composition also includes a disinfectant such as chlorhexidine, or a quaternary ammonium compound or an iodine compound such as povidone iodine. Chlorhexidine is the preferred disinfectant. The disinfectant is present in an amount of about 0.1 to 5.0% by weight of the total composition.

Other components which may be employed in the composition include a lower alkanol of 3 carbon atoms or less such as ethanol in an amount of about 0 to 75% by weight of the composition. Glycerine or other water soluble emollient such as sorbitol or water-dispersible lanolin may also be included, in an amount of about 0 to 75% by weight of the composition. The emollient serves to prevent chapping of the teats and to protect the tissue at the end of the teats as well as a propellant carrying agent. Either one or a combination of the alkanol and the emollient must be present in the amount of not less than 5% by weight.

The composition may also include a dye material to provide an indication that a particular cow has been treated in accordance with the invention. Suitable dyes which may be employed include water soluble, non-toxic dyes such as the conventional FD & C dyes. A particular dye which may be employed is FD & C Blue No. 1, and the amount of dye in the total composition will generally be less than 1.0% by weight.

Water is added in an amount sufficient to provide a total composition of 100 weight %.

Other components may be optionally added, such as suitable corrosion inhibitors, such materials being particularly desirable when a tin plate container is used to dispense the composition.

In one embodiment of the invention, the following composition was prepared:

| Component | Amount in Weight % |
| --- | --- |
| Chlorhexidine acetate | 0.4 |
| Dimethyl ether | 35.0 |
| SDA40-2 Ethyl alcohol, anhydrous | 10.0 |
| Glycerine USP 99% | 9.83 |
| FD & C Blue No. 1 | 0.003 |
| Water, deionized | 44.767 |
|  | 100% |

The composition of the present invention may be prepared by mixing all the components except the propellant and adding such mixture to a suitable container to be pressurized, after which the propellant is added under suitable pressurized conditions in accordance with conventional methods which are known in the art. Thus, for example, in the case of dimethyl ether, a supply of the propellant in liquid form at a pressure of 500 to 800 psi may be added to a container of the other mixed components to produce a pressurized container holding a homogeneous mixture of propellant and the other components, with an internal pressure of about 60 psi in the container.

The method of the present invention has been found to be particularly effective when a temperature in the range of from about 25° to 35° F. is rapidly attained on the exterior surface and orifice end of the teat 12 of the cow. Such a temperature should be obtained for at least approximately one second duration in order to achieve proper contraction of the sphincter 26. In general, the reduction of temperature on the teat surface adjacent the teat orifice 24 should be a value as cold as practical without creating tissue damage, preferably close to or slightly below the freezing temperature of water. The composition of the present invention has been found to provide such temperatures when applied as an aerosol spray 14 described herein. Such surface temperatures have been measured in the use of the present composition by a conventional surface temperature measuring probe placed on the surface of the teat adjacent the teat orifice 24 at the lower end of the teat 12. Application of the aerosol spray for less than about one second may not provide the desired chilling effect to cause proper contraction of the sphincter, whereas application of spray for periods of time greater than approximately one second may not be economically feasible since unnecessarily large amounts of disinfectant and other materials would be required.

The present composition has been found to be particularly effective in allowing the propellant component of the composition to disperse the disinfectant in an even manner throughout the spray pattern and also to allow a continuous ratio of these components to be obtained in the spray which is emitted from the can, from the first use of the can to the last.

It has been found by the present invention that cows are not unusually sensitive to the application of cold or chilling to the teat. Furthermore, it has been found that chilling of the teat at the indicated temperatures does in fact cause contraction of the sphincter muscle at the lower end of the teat orifice. This has been demonstrated by chilling the teat of a cow that is leaking milk due to milk letdown prior to milking. The chilling action at a chilling temperature in the range of about 25° to 35° F. will either stop or significantly slow down the leakage of milk. Such results have been obtained by the use of the aerosol spray of the invention on the teats of dairy cows both prior to and after milking.

The prepackaged form of the aerosol teat disinfectant, in accordance with the present invention, because of the hermetically sealed nature of the aerosol product eliminates contamination of the disinfectant prior to or during use. The standard dip cup on the farm, on the other hand, is often found to contain gross contamination. In the present invention, nothing but the spray composition with the uncontaminated disinfectant touches the teat. This eliminates cross-infection from cow to cow as frequently happens when the rim of the dip cup or other disinfectant applying instrument touches the end of the teat, easily spreading infection from cow to cow.

The containerized composition with teat disinfectant of the present invention provides a convenient form of teat disinfectant. It is easy to use and readily accepted by the farmer and the cow. The nuisance of having to repeatedly refill a dip cup is eliminated. Also the present aerosol spray provides a uniform application right up until the can is empty, which condition is apparent to the operator. With a dip cup, an operator may not apply any disinfectant to some teats as the cup becomes nearly empty.

It has also been found that an aerosol does a better job of applying the disinfectant to the teat. The force of the aerosol tends to blow away the residual drop of milk at the end of the teat. Also, the effervescence of the aerosol disinfectant tends to more readily penetrate the somewhat dilated teat orifice, which may take as long as two hours to close following a mechanical milking operation. This effervescent action provides more intimate contact of disinfectant at the teat orifice where the entry of infection usually occurs.

The chilling effect of the aerosol on the end of the teat is also very beneficial so far as promoting healthy tissue is concerned. The aerosol composition of the present invention is capable of chilling the teat surface to 30° F. Chilling tends to reduce the inflammation and edema caused by the trauma of the milking machine. Thus healthier tissue is obtained at the end of the teat and tissue in such condition can more readily prevent infection from entering the mammary gland. Chilling of the end of the teat also enhances contraction of the dilated sphincter muscle at the end of the teat. This also reduces the possibility of infection entering a mammary gland.

With regard to the composition of the present invention, considerable inventive effort was required to develop an aerosol formulation that would give a sprayed surface temperature effect in the range of about 25° to 35° when the content of the aerosol package were at ambient temperature. Such a characteristic was obtained by the use of the particular composition of the present invention which is a preferred composition.

By the present invention, there is provided a new improved method, composition and containerized product for use in preventing the infection of mastitis in dairy cows and other animals. No other disease in dairy cows has been as thoroughly investigated as mastitis, and it has been shown that for every dollar invested by the dairy farmer in mastitis control, more than eight dollars can be returned through improved production. Further, in herds where no control is attempted, it has been found that fifty percent of the cows are infected in an average of two quarters of the udder and three of every four cows are infected for seventy five percent of their milking lives. It has also been determined that an absolutely essential element in any effective effort to control mastitis is the application of disinfectant to the teats after each milking. New infections have been found to be reduced fifty percent or more when teats are treated with an appropriate disinfectant. Thus the persent invention provides a new and improved treatment in controlling and preventing a widely prevalent disease in dairy cows.

Figure 7:
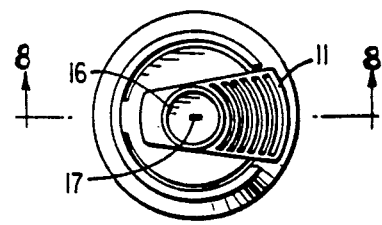
Figure 8:
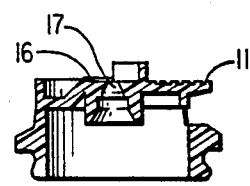

While the basic structure of the container 10, the valving component and cap 11 and the discharge nozzle component 16 with slot-shaped orifice, as illustrated in FIGS. 6–8 (which are drawn to scale) are well known and commercially available, the actual dimensions of the container, which is cylindrical, are approximately 7 inches (178 mm) in length from base to capped end and 2 inches (50 mm) in diameter. These dimensions provide a container which will have a capacity for at least 10 oz. of the composition and yet can be conveniently held by the dairy farmer while enabling enhanced directional applications of the spray.

The invention ma be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A containerized product for use in preventing mastitis in dairy cattle and other animals, comprising: a container capable of being pressurized, said container having a valve means including an orifice nozzle discharge device capable of directing a disinfectant composition outwardly from said container; and a water based disinfectant composition contained within said container and being useful in the treatment of mastitis, said composition consisting essentially of a homogeneous mixture of: about 0.1 to 5.0 weight % of a disinfectant; about 5 to 75 weight % of a water and alcohol soluble aerosol propellant carrier having the characteristic of low temperature production upon volatilization; about 0 to 75 weight % of a lower alkanol; about 0 to 75 weight % of a water soluble emollient, either one or a combination of the alkanol and emollient being present in an amount of not less than 5 weight %; up to 1.0 weight % of a water soluble dye; and water in an amount sufficient to provide a total composition of 100 weight %; said mixture being uniformly homogeneous throughout the use thereof.

2. The product of claim 1, wherein said disinfectant is chlorhexidine.

3. The product of claim 1, wherein said propellant is dimethyl ether.

4. The product of claim 1, wherein said container is made from aluminum.

5. The product of claim 4, wherein a coating lines the interior of said container.

6. The product of claim 1, wherein said container is made from tin-plate.

7. The product of claim 6, wherein said composition further includes a corrosion inhibitor container.

8. The product of claim 1, wherein said container is elongate and cylindrical and said valve means includes orifice nozzle means for directing an aerosol spray axially outwardly from one end of said container in a fan-shaped pattern.

9. The product of claim 1, wherein said container is elongate and cylindrical having a diameter of approximately 50 mm and a length of approximately 178 mm providing a chamber for containing approximately 280 grams (10 oz.) of said composition.

10. The product of claim 1, wherein a coating lines the interior of said container.

11. A water based disinfectant composition adapted for storage in a pressurized environment and useful in the prevention of mastitis when applied as an aerosol spray to the outer skin surface of a teat of a mammal, whereby said outer skin surface is chilled to a surface temperature of about 25° to 35° F., said composition consisting essentially of a homogeneous mixture of: about 5 to 75 weight % of a water and alcohol soluble aerosol propellant; about 0.1 to 5.0 weight % of a disinfectant; about 0 to 75 weight % of a lower alkanol; about 0 to 75 weight % of a water soluble emollient, either one or a combination of the alkanol and emollient being present in an amount of not less than 5 weight %; up to 1.0 weight % of a water soluble dye; and water in an amount sufficient to provide a total composition of 100 weight %; said mixture being uniformly homogeneous throughout the use thereof.

12. The composition of claim 11 wherein said propellant is dimethyl ether.

13. The composition of claim 11 wherein said disinfectant is chlorhexidine.

14. A water based disinfectant composition adapted for storage in a pressurized environment and useful in the prevention of mastitis when applied as an aerosol spray to the outer skin surface of a teat of a mammal, consisting essentially of a homogeneous mixture of: about 5 to 75 weight % of dimethyl ether; about 0.1 to 5.0 weight % of a disinfectant; about 0 to 75 weight % of a lower alkanol; about 0 to 75 weight % of a water soluble emollient, either one or a combination of the alkanol and emollient being present in an amount of not less than 5 weight %; up to 1.0 weight % of a water soluble dye; and water in an amount sufficient to provide a total composition of 100 weight %; said mixture being uniformly homogeneous throughout the use thereof.

15. The composition of claim 14 wherein said disinfectant is chlorhexidine.

* * * * *

UNITED STATES PATENT AND TRADEMARK OFFICE
CERTIFICATE OF CORRECTION

PATENT NO. : 4,716,032

DATED : December 29, 1987

INVENTOR(S) : GEOFFREY WESTFALL & FRANKLIN D. HASSE

It is certified that error appears in the above-identified patent and that said Letters Patent is hereby corrected as shown below:

In the Claims:

Column 7, line 51, Cancel "container".

Signed and Sealed this

Twenty-fourth Day of May, 1988

Attest:

DONALD J. QUIGG

*Attesting Officer*      *Commissioner of Patents and Trademarks*